(12) United States Patent
Georgeson et al.

(10) Patent No.: US 7,050,535 B2
(45) Date of Patent: May 23, 2006

(54) X-RAY LAMINOGRAPHY INSPECTION SYSTEM AND METHOD

(75) Inventors: Gary E. Georgeson, Federal Way, WA (US); Morteza Safai, Seattle, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 11/045,861

(22) Filed: Jan. 28, 2005

(65) Prior Publication Data

US 2006/0056585 A1  Mar. 16, 2006

Related U.S. Application Data

(63) Continuation-in-part of application No. 10/943,088, filed on Sep. 16, 2004.

(51) Int. Cl.
*G01N 23/04* (2006.01)
(52) U.S. Cl. .......................................... 378/57; 378/21
(58) Field of Classification Search ............ 378/57–58, 378/21–27, 20, 68, 41, 196–197; 324/261
See application file for complete search history.

(56) References Cited

U.S. PATENT DOCUMENTS

| | | | |
|---|---|---|---|
| 2,005,035 A | 6/1935 | Houtman |
| 4,010,636 A | 3/1977 | Clark et al. |
| 4,045,678 A | 8/1977 | Rickard |
| 4,117,733 A | 10/1978 | Gugel |
| 4,167,880 A | 9/1979 | George |
| 4,311,052 A | 1/1982 | Jeffras et al. |
| 4,399,703 A | 8/1983 | Matzuk |
| 4,466,286 A | 8/1984 | Berbeé et al. |
| 4,612,808 A | 9/1986 | McKirdy et al. |
| 4,807,476 A | 2/1989 | Cook et al. |
| 5,062,301 A | 11/1991 | Aleshin et al. |
| 5,593,633 A | 1/1997 | Dull et al. |
| 5,902,935 A | 5/1999 | Georgeson et al. |
| 6,167,110 A | 12/2000 | Possin et al. |
| 6,459,759 B1 * | 10/2002 | Tominaga .................... 378/22 |
| 6,484,583 B1 | 11/2002 | Chennell et al. |
| 6,507,635 B1 | 1/2003 | Birdwell et al. |
| 6,658,939 B1 | 12/2003 | Georgeson et al. |
| 6,711,235 B1 | 3/2004 | Galish et al. |

(Continued)

FOREIGN PATENT DOCUMENTS

EP    1 193 491 A2    4/2002

(Continued)

OTHER PUBLICATIONS

*Automated Ultrasonic Sanning System (AUSS®), Mobile Automated Scanner (MAUS®)* http://www.engineeringatboeing.com/mfgquality/quality/automatedsystems.html, Jun. 21, 2004, 4 pages.

(Continued)

*Primary Examiner*—David V. Bruce
*Assistant Examiner*—Hoon Song
(74) *Attorney, Agent, or Firm*—Alston & Bird LLP (57) ABSTRACT

For inspecting a structure with non-destructive x-ray laminography inspection, probes are magnetically coupled to opposing surfaces of the structure. The probes include an x-ray source and an x-ray detector which are driven to obtain inspection data that facilitates x-ray laminographic inspection of the structure. A device may be autonomous with a feedback-controlled motor and/or a positional encoder for translation of the probes. A device may include wireless operation. A display may be included to provide real-time visual images of the x-ray laminography or position information.

25 Claims, 2 Drawing Sheets

U.S. PATENT DOCUMENTS

| | | | |
|---|---|---|---|
| 6,722,202 | B1 | 4/2004 | Kennedy et al. |
| 6,748,791 | B1 | 6/2004 | Georgeson et al. |
| 2003/0154801 | A1 | 8/2003 | Georgeson |
| 2003/0210027 | A1* | 11/2003 | Pedigo et al. ............... 324/67 |
| 2004/0037393 | A1 | 2/2004 | Birdwell et al. |
| 2004/0103721 | A1 | 6/2004 | Georgeson |

FOREIGN PATENT DOCUMENTS

| | | |
|---|---|---|
| GB | 2 023 380 A | 12/1979 |

OTHER PUBLICATIONS

*Inspection of In-Service Composite-Honeycomb Structures,* Aerospace Application Note, Rev.: 2002-01, R/D Tech.

*Probe Catalog 2003-2004,* Thru-Transmission Ultrasonics, NDT Engineering Corporation, R/D Tech Company, pp. 1-11.

*Air-Coupled Ultrasonic Inspection,* http://www.gmi-inc.com/airscan.htm, Aug. 19, 2004, 3 pages.

U.S. Appl. No. 10/734,452, filed Dec. 12, 2003, In. re: Bossi et al., entitled *Ultrasonic Inspection Device for Inspecting Components at Preset Angles.*

U.S. Appl. No. 10/752,890, filed Jan. 7, 2004, In re: Bossi et al., entitled *Non-Destructive inspection Device for Inspecting Limited-Access Features of a Structure.*

U.S. Appl. No. 10/943,088, filed Sep. 16, 2004, In re: Georgeson et al., entitled *Magnetically Attracted Inspecting Apparatus and method Using a Ball Bearing.*

U.S. Appl. No. 10/943,068, filed Sep. 16, 2004, In re: Georgeson et al., entitled *Apparatus and Method for Area Limited-Access Through Transmission Ultrasonic Inspection.*

U.S. Appl. No. 10/943,135, filed Sep. 16, 2004; In re: Georgeson et al., entitled *Magnetically Attracted Inspecting Apparatus and Method Using a Fluid Bearing.*

U.S. Appl. No. 10/943,170, filed Sep. 16, 2004; In re: Georgeson et al., entitled *Alignment Compensator for Magnetically Attracted Inspecting Apparatus and Method.*

U.S. Appl. No. 10/943,045; filed Sep. 16, 2004; In re: Wright et al., entitled *End Effector Inspection Apparatus and Method.*

U.S. Appl. No. 11/041,499, filed Jan. 24, 2005; In re: Kennedy et al., entitled *Non-Destructive Stringer Inspection Apparatus and Method.*

U.S. Appl. No. 11/041,601, filed Jan. 24, 2005; In re: Safai et al., entitled *Real-Time X-Ray Scanner and Remote Crawler Apparatus and Method.*

* cited by examiner

X-RAY LAMINOGRAPHY INSPECTION SYSTEM AND METHOD

CROSS-REFERENCE TO RELATED APPLICATIONS

This application is a continuation-in-part of co-pending application Ser. No. 10/943,088, entitled "Magnetically Attracted Inspecting Apparatus and Method Using a Ball Bearing," filed Sep. 16, 2004. The contents of U.S. Pat. No. 6,722,202 and co-pending application Ser. No. 10/752,890, entitled "Non-Destructive Inspection Device for Inspection Limited-Access Features of a Structure," filed Jan. 7, 2004, application Ser. No. 10/943,170, entitled "Alignment Compensator for Magnetically Attracted Inspecting Apparatus and Method," filed Sep. 16, 2004, application Ser. No. 11/041,499, entitled "Non-Destructive Stringer Inspection Apparatus and Method," filed Jan. 24, 2005, and application Ser. No. 11/041,601, entitled "Real-Time X-Ray Scanner and Remote Crawler Apparatus and Method," filed Jan. 24, 2005, are incorporated by reference.

FIELD OF THE INVENTION

The present invention relates generally to an apparatus and method for inspecting a structure and, more particularly, to an apparatus and method for non-destructive x-ray inspection of a structure.

BACKGROUND

Non-destructive inspection (NDI), also referred to as non-destructive evaluation (NDE) and non-destructive testing (NDT), of structures involves thoroughly examining a structure without harming the structure or requiring its significant disassembly. Non-destructive inspection is typically preferred to avoid the schedule, labor, and costs associated with removal of a part for inspection, as well as avoidance of the potential for damaging the structure. Non-destructive inspection is advantageous for many applications in which a thorough inspection of the exterior and/or interior of a structure is required. For example, non-destructive inspection is commonly used in the aircraft industry to inspect aircraft structures for any type of internal or external damage to or flaws in the structure. Inspection may be performed during manufacturing or after the completed structure has been put into, including field testing, to validate the integrity and fitness of the structure. In the field, access to the interior surfaces of the structure is often restricted, requiring disassembly of the structure, introducing additional time and labor.

Among the structures that are routinely non-destructively tested are composite structures, such as composite sandwich structures and other adhesive bonded panels and assemblies including carbon fiber or graphite reinforced epoxy (Gr/Ep) and non-ferromagnetic metals (e.g. aluminum alloy, titanium alloy, or aluminum or titanium hybrid laminates such as GLARE or Ti/Gr). In this regard, composite structures are commonly used throughout the aircraft industry because of engineering qualities, design flexibility, low weight, and high stiffness-to-weight ratio. A shift toward bonded materials dictates that devices and processes are available to ensure structural integrity, production quality, and life-cycle support for safe and reliable use. As such, it is frequently desirable to inspect composite structures to identify any flaws, such as cracks, voids or porosity, which could adversely affect performance. For example, typical flaws in composite sandwich structures, generally made of one or more layers of lightweight honeycomb or foam core material with composite or metal skins bonded to each side of the core, include disbonds which occur at the interfaces between the core and the skin or between the core and a buried septum.

Various types of sensors may be used to perform non-destructive inspection. One or more sensors may move over the portion of the structure to be examined, and receive data regarding the structure. For example, a pulse-echo (PE), through transmission (TT), or shear wave sensor may be used to obtain ultrasonic data, such as for thickness gauging, detection of laminar defects and porosity, and/or crack detection in the structure. Resonance, pulse echo or mechanical impedance sensors may be used to provide indications of voids or porosity, such as in adhesive bond-lines of the structure. High resolution inspection of aircraft structure is commonly performed using semi-automated ultrasonic testing (UT) to provide a plan view image of the part or structure under inspection. While solid laminates may be inspected using one-sided pulse echo ultrasonic (PEU) testing, composite sandwich structures typically require through-transmission ultrasonic (TTU) testing for high resolution inspection. In through-transmission ultrasonic inspection, ultrasonic sensors such as transducers, or a transducer and a receiver sensor, are positioned facing each other but contacting opposite sides of the structure. An ultrasonic signal is transmitted by at least one transducer, propagated through the structure, and received by the other transducer. Data acquired by the sensors is typically processed and then presented to a user via a display as a graph of amplitude of the received signal. To increase the rate at which the inspection of a structure is conducted, a scanning system may include arrays of inspection sensors, i.e., arrays of transmitters and detectors. As such, the inspection of the structure can proceed more rapidly and efficiently, thereby reducing the costs associated with the inspection.

Many structures are difficult to accurately inspect using PE or TTU scanning. X-ray inspection may be preferred for certain situations because of the high flaw resolution and ability to image flaws that are not parallel to the surface and without the use of a couplant. X-ray inspection could be used for close-out inspection of bonded wings, spar e-beams, complex composite sandwich structures, complex laminate composites, titanium graphite (Ti/Gr) materials, and fiber-reinforced metal-matrix composites (MMCs). Conventional x-ray inspection systems expose film that is developed to create an image that can be analyzed visually. Recently, CCD (charge coupled device) and CMOS (complementary metal oxide semiconductor) detectors have been used for the imaging, rather than film. Traditional 2-D inspection techniques, however, produce a projection of 3-D space into 2-D; thus, objects are superimposed and depth information is lost. And although ultrasonic pulse-echo inspection is able to retain depth information, near-surface features and flaws can mask other features and flaws further from the surface of the structure. In addition, the image resolution obtained using ultrasonic pulse-echo inspection may not be high enough for some applications, and flaws parallel to the inspection signals may be difficult to find and identify.

Non-destructive inspection may be performed manually by technicians who typically move an appropriate sensor over the structure. Manual scanning generally consists of a trained technician holding a sensor and moving the sensor along the structure to ensure the sensor is capable of testing all desired portions of the structure. However, typical x-ray inspection applications operate with high power emissions which prevent manual operation.

Semi-automated inspection systems have been developed to overcome some of the shortcomings with manual inspection techniques. For example, the Mobile Automated Scanner (MAUS®) system is a mobile scanning system that generally employs a fixed frame and one or more automated scanning heads typically adapted for ultrasonic inspection. A MAUS system may be used with pulse-echo, shear wave, and through-transmission sensors. The fixed frame may be attached to a surface of a structure to be inspected by vacuum suction cups, magnets, or like affixation methods. Smaller MAUS systems may be portable units manually moved over the surface of a structure by a technician. However, for through-transmission ultrasonic inspection and x-ray inspection, a semi-automated inspection system requires access to both sides or surfaces of a structure which, at least in some circumstances, will be problematic, if not impossible, particularly for semi-automated systems that use a fixed frame for control of automated scan heads.

Automated inspection systems have also been developed to overcome the myriad of shortcomings with manual inspection techniques. For example, the Automated Ultrasonic Scanning System (AUSS®) system is a complex mechanical scanning system that employs through-transmission ultrasonic inspection. The AUSS system can also perform pulse echo inspections, and simultaneous dual frequency inspections. The AUSS system has robotically controlled probe arms that must be positioned proximate the opposed surfaces of the structure undergoing inspection with one probe arm moving an ultrasonic transmitter along one surface of the structure, and the other probe arm correspondingly moving an ultrasonic receiver along the opposed surface of the structure. Another example robotic system is the x-ray inspection system used at the William-Gateway Structural Repair Facility in Mesa, Ariz., for inspection of F-18 tail sections. Conventional automated scanning systems, such as the AUSS-X system and the William-Gateway x-ray system, therefore require access to both sides or surfaces of a structure which, at least in some circumstances, will be problematic, if not impossible, particularly for very large or small structures. To maintain the transmitter and receiver in proper alignment and spacing with one another and with the structure undergoing inspection, the AUSS-X system has a complex positioning system that provides motion control in ten axes.

Conventional x-ray inspection systems are gantry systems. Many parts, however, are too large for examination; the system cannot reach the full extent of the part because the scan envelope of the system is limited. Further, conventional NDI systems are not designed to provide detailed information about internal features of a structure, particularly with respect to internal damage or flaws that are parallel to an inspection signal.

SUMMARY OF THE INVENTION

The present invention provides an improved apparatus and method for inspecting a structure and is the laminographic counterpart of the ultrasound system described in application Ser. No. 10/943,088. Embodiments of the present invention combine x-ray inspection technologies with magnetically coupled inspection probe technologies to provide x-ray inspection devices that are portable, can be used for various applications, and provide inspection results in real-time. In addition, embodiments of the present invention provide digital laminography. An embodiment of the present invention can collect x-ray attenuation information from multiple projections and digitally construct data representing density slices of the interior of a structure to produce a 3-D display of the interior of the structure. Depending on the particular x-ray laminography inspection technique, a corresponding reconstruction algorithm is used to perform the digital reconstruction of the 3-D inspection data. Such devices can provide high resolution flaw detection in structures of varying shapes and sizes, including metal and composite structures such as bondlines, weldlines, and lap joints. Embodiments of apparatus and methods of the present invention can be used for inspection of structures during manufacture or in-service. Accordingly, embodiments of the present invention can replace or reduce the need for conventional inspection techniques, including film-based x-ray inspection techniques and large, expensive fixed inspection robots and gantries, thereby reducing the cost of structural integrity inspection. Further, embodiments of the present invention provide new inspection capabilities for x-ray inspection of large and small structures, structures with limited-access features, and complex features of structures.

Apparatus and methods of the present invention use magnetically coupled probes including respective sensing elements, such as an x-ray source and an x-ray detector, that are disposed proximate opposed surfaces of a structure. Additionally, methods and apparatus of the present invention are capable of operating in array modes, thereby increasing inspection speed and efficiency while reducing cost.

For continuous scanning applications, only one probe need be driven due to the magnetic coupling between the probes. Thus, methods and apparatus of the present invention are advantageously adapted in a leader-follower relationship to inspect structures in which one surface of the structure is relatively inaccessible or structures which are exceptionally large. Further, embodiments of methods and apparatus of the present invention permit the probes to contact and ride along the respective surfaces of the structure, thereby reducing or eliminating the necessary sophistication of a motion control system that is typically required by conventional scanning systems to maintain the probes in a predefined orientation with respect to each other and at a predefined spacing from the respective surface of a structure undergoing inspection. Permitting the probes to contact and ride along the respective surfaces of the structure also may maintain alignment between the probes and/or the x-ray sensors of the probes. Contact with the surface also permits accurate position measurement of the inspection device during continuous scanning, such as keeping an optical or positional encoder in physical and/or visual contact with the surface of the structure under inspection. One probe likely includes an encoder so that it can tell its position or, perhaps, differential GPS. In such a way, it can record or transmit data to record where flaws are located during continuous inspection.

Embodiments of the present invention also provide for wireless inspection operation. By wirelessly transmitting inspection data, such as digital images from x-ray detectors, a probe operating on battery power can be free of all wired connections for power or data transmission.

A non-destructive inspection apparatus of the present invention for inspecting a structure includes two probes which are configured for being positioned on separate surfaces of the structure. Each probe includes at least one magnetic coupling device for magnetically coupling the probe with the other. The magnetic coupling between the probes causes movement of both probes when only one probe is driven. One probe includes an x-ray source for inspecting the structure. The other probe includes at least one x-ray detector for receiving radiation from the x-ray source. The probes including the x-ray source and detector may perform x-ray laminography inspection of the structure when the probes are fixed in position or moving over opposing surfaces of the structure. The probes may also adjust the incident angle of radiation from the x-ray source. In addition, probes may include motors for moving the probes and/or controlling rotational and/or translational movement of the x-ray source and detector, motion mechanisms for supporting this rotational and/or translational movement of the x-ray source and detector, and vacuum suction cups for affixing the probes to the structure. A probe may also include a wireless transmitter for transmitting x-ray inspection data. The apparatus may include a display for presenting x-ray inspection images captured by the x-ray detector and a computer for reconstructing x-ray attenuation data.

A method of the present invention of inspecting the structure includes the steps of supporting probes on opposite surfaces of the structure, establishing magnetic attraction between the probes, and inspecting the structure using an x-ray laminography technique by repeatedly transmitting x-ray inspection signals from an x-ray source carried by one probe into the structure and receiving x-ray inspection signals following propagation through the structure by an x-ray detector carried by the other probe. Other embodiments include moving the x-ray source and/or the probes, displaying x-ray inspection data, and/or wirelessly transmitting x-ray inspection data. Another method includes adjusting the incident angle of the x-ray inspection signals from the x-ray source.

DETAILED DESCRIPTION

The present invention will be described more fully with reference to the accompanying drawings. Some, but not all, embodiments of the invention are shown. The invention may be embodied in many different forms and should not be construed as limited to the described embodiments. Like numbers refer to like elements and parameters throughout the drawings.

The present invention provides an improvement of co-pending application Ser. No. 11/041,601, entitled "Real-Time X-Ray Scanner and Remote Crawler Apparatus and Method," filed Jan. 24, 2005. Because many features of structures are layered and/or have features at various depths, internal damage to structures or elements of structures may be advantageously perceived and/or interpreted for analysis by the results of x-ray laminography inspection. Embodiments of the present invention provide systems and methods for x-ray laminography, including magnetically coupled, portable systems that perform laminographic inspection at a fixed location and may optionally also move across a structure for further inspection; portable systems that perform laminographic inspection over an area of a structure using a magnetically coupled inspection bridge such as a system that incorporates a probe with an x-y plotter mechanism to move the x-ray source and x-ray detector over the area of the structure during the laminographic inspection; and portable systems that perform laminographic inspection of a structure from the movement of magnetically coupled probes across the structure. Unlike conventional x-ray computed tomography (CT) that requires substantial access to a part such as 360 degree revolution around a part, embodiments of the present invention employing x-ray laminography and using magnetically coupled probes can perform inspection of large, planar, and/or limited-access structures.

X-ray laminography techniques typically involve an x-ray source and x-ray detector moving in synchronous circles or translating in opposite directions, which are also referred to as classical rotational and translational laminography. Laminography may be performed in other manners, such as complex-motion laminography involving both rotational and translational laminography, computed laminography (CL) involving linear translation of the x-ray source and x-ray detector with respect to the structure but where the x-ray source and x-ray detector remain respectively stationary with respect to each other, and multi-point laminography involving reconstruction of x-ray attenuation data from multiple projections of a structure or features taken at arbitrary positions and/or angles. These and other laminography inspection techniques, including currently known and later developed laminography inspection techniques, can be used by embodiments of the present invention to provide magnetically coupled x-ray inspection probes capable of performing non-destructive x-ray laminographic inspection of a structure. Generally, laminography takes advantage of the fact that objects in the focal plane of an x-ray inspection signal are captured clearly on film or by an x-ray detector while objects not in the focal plane are only captured as background noise. By repeating the process and capturing x-ray attenuation data for multiple focal planes, a 3-D representation can be formed from the multiple plane images, such as representing the multiple plies of a laminate structure. When using a digital x-ray detector rather than film, x-ray attenuation data of multiple plane images from various discrete projections of the structure can be combined by a computer to produce a 3-D digital representation of the inspection of the structure. Further, when using a digital x-ray detector, a computer can perform reconstruction of the projection data by removing the background noise, thereby providing higher contrast resolution of the inspection data. X-ray laminography techniques are further described in *Digital Computed Laminography and Tomosynthesis—Functional Principals and Industrial Applications* by S. Gondrom and S. Schropfer from the Proceedings of the International Symposium on Computerized Tomography for Industrial Applications and Image Processing in Radiology, Berlin, Germany, published in BB 67-CD by DGZfP (Mar. 15–17, 1999) and by NDT.net, Vol. 4, No. 7 (July 1999).

One advantage of performing x-ray laminography inspection is that the result provides reconstructed layer-by-layer imaging of the structure under inspection such as multi-ply composite materials and elements of the structure under inspection such as bonded joints. Accordingly, x-ray attenuation information from multiple projections can be viewed by individual digitally reconstructed density slices of the interior of the structure or viewed as a 3-D model display of the structure.

Figure 1A:
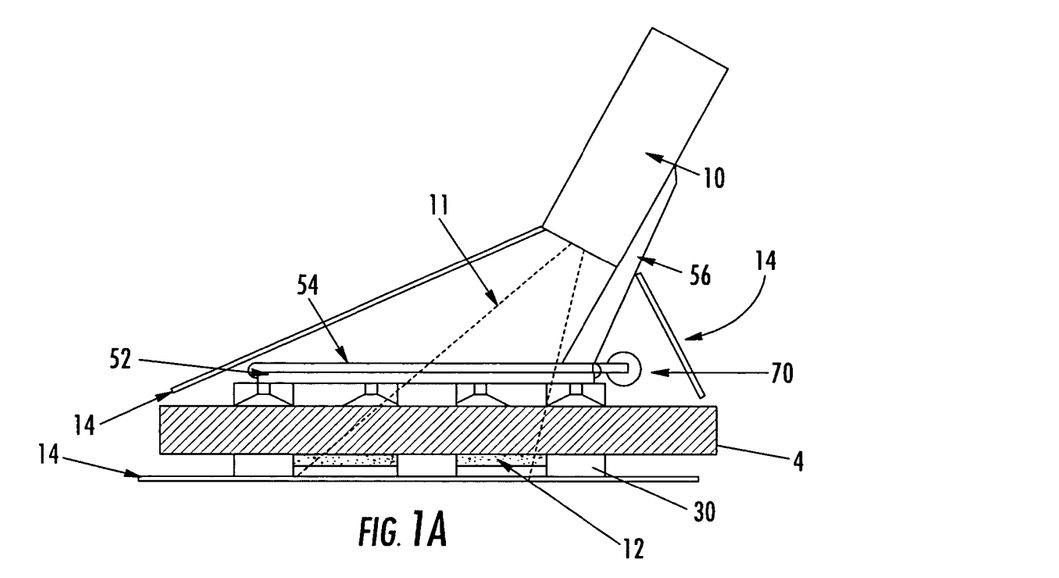
FIG. 1A is a schematic diagram of an inspection apparatus.
Figure 1B:
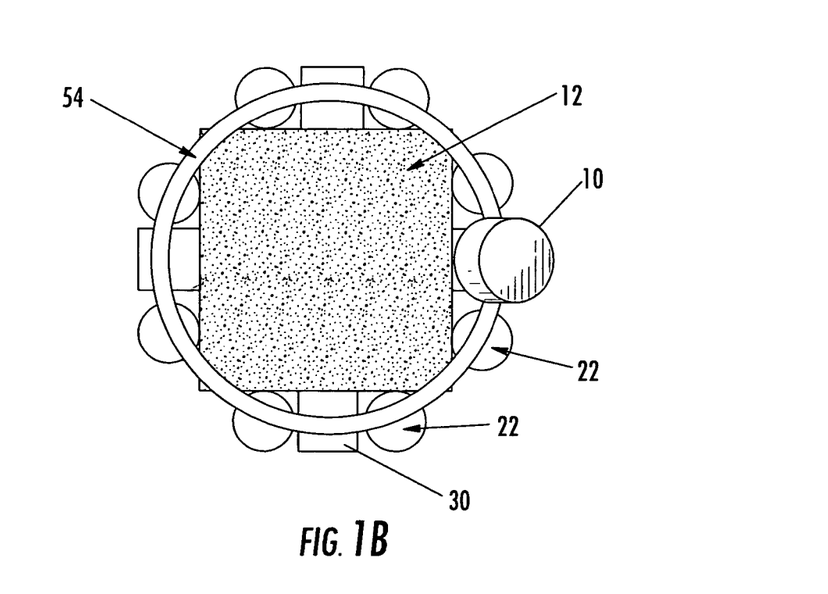
FIG. 1B is a schematic diagram of the apparatus of FIG. 1A.
Figure 2:
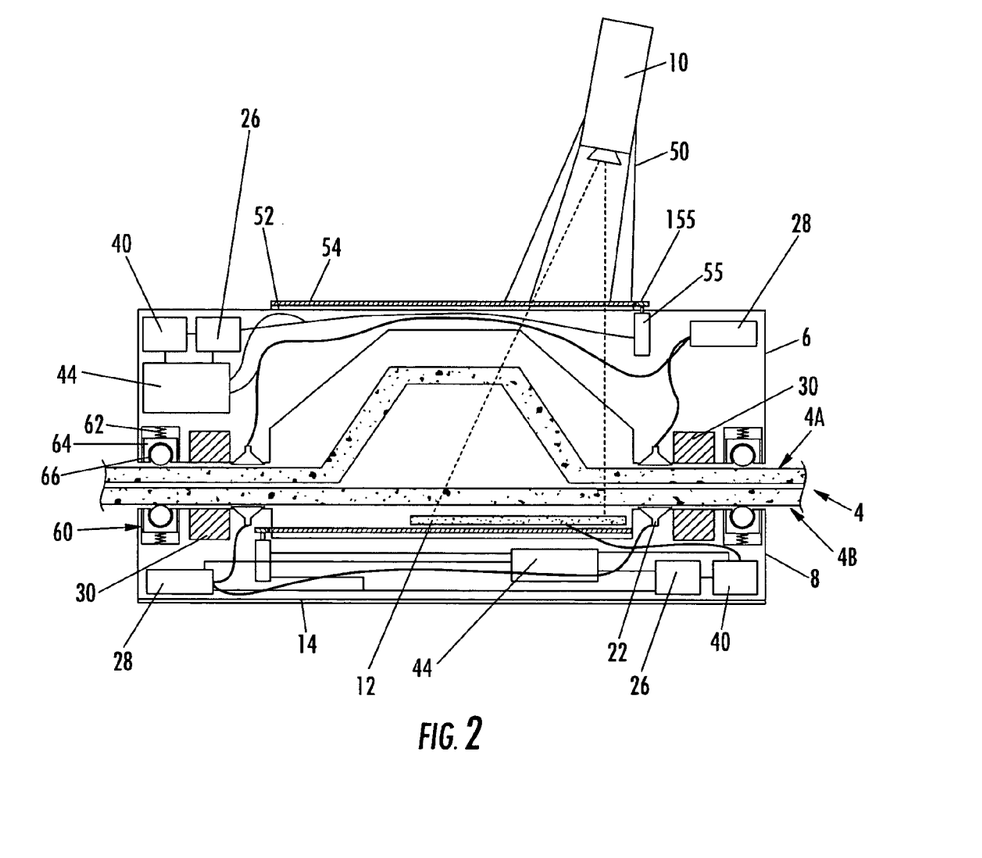
FIG. 2 is a schematic diagram of another inspection apparatus.

By using embodiments of the present invention, digital x-ray laminography techniques are portable and can be used for NDI inspection of various structures. Further, because of the magnetic coupling of probes, x-ray laminography can be performed on limited-access structures. And because of the ability to position and move magnetically coupled probes, different x-ray laminography techniques are available for NDI inspection, including rotation, translation, and simultaneous rotation and translation of the x-ray source and/or x-ray detector with appropriate mechanisms and controls. The embodiment of FIGS. 1A and 1B is an example where the x-ray source is rotated, and the embodiment of FIG. 2 is an example where the x-ray source and x-ray detector are simultaneously rotated.

Embodiments of the present invention can accomplish versatile high resolution x-ray inspection systems by integrating an x-ray source, such as a microfocus x-ray source, with an x-ray detector, such as a complementary metal oxide semiconductor (CMOS) detector, using probes that also include magnetically coupled devices. One probe includes the microfocus x-ray source and a magnetically coupled device, while the other probe includes the real-time x-ray detector and the other magnetically coupled device. The probes may be positioned on opposite sides of the structure under inspection. This configuration allows for real-time inspection with simple alignment of the x-ray source and the x-ray detector using the magnetic coupling between the probes. Further, the magnetic coupling of the probes allows for moving the inspection apparatus along the structure for inspection of large and complex composite, metal, and ceramic structures.

A microfocus x-ray source can produce less than one micrometer (μm) diameter focal spot size along the axis of the x-ray beam at approximately 162 kilovolts (kV) energy with an x-ray tube current of 200 microamps (μA). The functional capabilities of microfocus x-ray sources therefore allow for high resolution, nondestructive inspection of structures, including structures which would otherwise be too thick for conventional inspection using pulse echo or through transmission ultrasonic inspection. In addition, microfocus x-ray sources generate less scattered ionizing radiation than conventional x-ray sources. Further, the use of a microfocus x-ray tube realizes a low-dose x-ray inspection technology that reduces the safety issues related to conventional radiographic inspection. For example, many composite structures can be inspected with x-ray beams with as low as 20 kiloelectronvolts (KeV) energy values. Using such equipment reduces shielding problems and allows operators to be in the area of the inspection operation.

Real time high resolution x-ray detectors, such as a CMOS detector, may be used in conjunction with an x-ray scintillator, such as a CsI, $Gd_2O_2S$ or $CaWO_4$ x-ray scintillator, for high resolution detecting capability. The use of CMOS detectors has several advantages, including relatively low cost, high resolution imaging capabilities because of small pixel size, and antiblooming capability, meaning that adjacent detectors will not saturate with intense illumination which occurs in CCD type detectors. Further, the amplification circuit and all necessary logic circuits and multiplexing may be integrated onto the CMOS detector chip to allow for high speed data transfer, shuttering, windowing, and asynchronizing of the CMOS detector. Although CMOS detectors may be preferred in many applications, an x-ray detector of the present invention can also be a CCD detector, amorphous selenium, amorphous silicon, or other silicon-based or solid-state linear or array detector. More generally, these detectors may be used without x-ray sensitive scintillators. Further, x-ray detectors may be connected to or include digital microprocessors and/or image processors with auto defect recognition.

While a portion of a relatively simple structure is depicted in FIG. 1, a structure being inspected may be any myriad of shapes and/or sizes and used in a variety of applications, including aircraft, marine vehicles, automobiles, spacecraft and the like, as well as buildings. Moreover, a structure may be inspected prior to assembly or following assembly, as desired.

Components for an x-ray scanner such as an x-ray source and an x-ray detector, may be supported on opposing surfaces of the structure and may include magnetically coupled probes, as described in co-pending application Ser. Nos. 10/943,088; 10/752,890; or 10/943,170. Alternatively, embodiments of the present invention may use magnetically coupled support structures for semi-automated NDI such as a support structure that permits a robotic plotter-type mechanism to provide scanning over an x-y coordinate plane defined by the area of the support structure similar to embodiments described in co-pending application Ser. No. 10/943,068. Additional embodiments of the present invention may use a robotic control system for single-sided control of magnetically coupled probes of such embodiments. Using magnetically coupled probes aligns the x-ray source and x-ray detector as required for the inspection. For example, a weldline may be inspected at 45° angle relative to the skin of the structure in which case the x-ray source, and possibly also the x-ray detector, could be oriented at an angle of 45° with respect to the skin. In such off-axis (non-perpendicular) orientation applications, the x-ray source and x-ray detector may not be aligned across from each other, but at corresponding positions such that the focus of the x-ray signals are transmitted from the x-ray source through the structure to the x-ray detector. In an embodiment of the present invention for such an application, the x-ray source, and possibly the x-ray detector, can be adjusted or set at a specific angle using a pivot point on the magnetically coupled probe. The specific angle for the x-ray source, and possibly x-ray detector, may be motor-controlled or manually adjusted.

Embodiments of the present invention may include wireless operation, such as wireless transmission of the digital x-ray images captured by the x-ray detector. Accordingly, at least one of the magnetically coupled probes, typically the probe supporting the x-ray detector, can be used without having to feed wires into the structure for transmission of the digital images, and possibly also for powering the device. In many situations, the wireless operation, and cordless capability, of an inspection probe may be advantageous, such as in a situation where the magnetically coupled probe and x-ray detector are used in limited access areas, such as inside a that stringer or along the inside of an internal bondline. To provide a completely wireless inspection probe, battery power may be used for any type of equipment which requires power, such as the x-ray detector and a wireless transmitter. A wireless transmitter may use any type of technology which permits transmission of the digital x-ray images captured by the x-ray detector, such as a cellular technology, Bluetooth wireless transmission, or optical means for wireless transmission of data. Wireless operation can also be provided where other elements of a probe are generated by battery power, such as operating a battery-powered x-ray source with a wireless controller. In addition, an optical imager may be used to provide visual identification of the internal position or feature of the structure under inspection to assist in the interpretation and/or location of the x-ray inspection probe on an opposing surface of the part. Having a real-time image allows for real-time inspection of the structure, and even re-inspection of an area of doubt. For example, an inspection probe located on the outside of a complex structure under inspection can include, in addition to the x-ray source, a display for displaying digital images captured by the x-ray detector or an optical imager of the magnetically coupled probe on the opposing surface of the structure. Permitting the technician to immediately view in real time the images captured by an x-ray detector or an optical imager of a magnetically coupled probe on the opposing surface of the structure may improve the inspection of the structure, such as by providing the technician the ability to interpret the location of the magnetically coupled probe and the images captured thereby.

In FIGS. 1A and 1B, an inspection apparatus includes an x-ray source 10 and an x-ray detector 12 for performing x-ray laminography for inspecting a septumized core material structure 4. Corresponding magnetically coupled probes are positioned on opposing surfaces of the structure 4 in order to support the x-ray source 10 and x-ray detector 12. In addition to the use of a low power x-ray source 10, such as a microfocus x-ray tube, x-ray shielding 14 can be used to provide further protection against unnecessary exposure to technicians. Magnetic coupling devices 30 carried by or otherwise associated with the probes provide the magnetic attraction required to support the probes on opposing surfaces of the structure 4. To maintain accurate positioning of the probes with respect to the structure 4, at least one probe may include suction cups 22, such as rubber suction cups connected to a vacuum pump or a like mechanism that provides fixed positioning of the probe with respect to the surface of the structure. The x-ray source 10 may be affixed to one of the probes using a support mechanism 56 such as a locking tube mount that attaches to a motion mechanism of the probe, such as a circular racer bearing 54 rotatably connected to a ring frame 52. Appropriately, the x-ray source 10 is capable of moving with respect to the structure 4 to perform x-ray laminographic inspection. A control device 70 such as a smart stepper motor may be used to control the motion of the x-ray source 10 with respect to the structure 4, such as controlling the motion mechanism when the x-ray source 10 is attached thereto to provide controlled movement of the x-ray source 10. A motion mechanism for classical rotational laminography typically may employ a ball or roller thrust bearing. Additional embodiments may use one or more ball or needle bearings and/or a track or groove to provide rotational and/or translational motion for an x-ray source or an x-ray detector. Any type of motion mechanism that can be controlled and for which position and/or incident angle information can be provided for use in digitally generating 3-D inspection data may be used.

In the embodiment shown in FIGS. 1A and 1B, the x-ray detector 12, such as an amorphous selenium, amorphous silicon, or other x-ray detector, may be maintained in a fixed position with respect to the structure 4 because it is sufficiently large enough to capture the x-ray attenuation information from the x-ray source 10 as the x-ray source 10 moves with respect to the structure 4. Alternatively, as shown with respect to the embodiment in FIG. 2, an x-ray detector may also move with respect to a structure and corresponding to the movement of the x-ray source for inspection applications such as NDI that requires a larger scanning area or a more acute incident angle of the x-ray inspection signal from the x-ray source.

In operation, a computer or other processing device can be used to control the activation of the x-ray source 10 and a smart stepper motor 70 that rotates the x-ray source 10. The smart stepper motor 70 may contain a positional encoder to provide feedback information regarding the position of the x-ray source 10 with respect to the structure 4. X-ray attenuation projections can be taken at different positions as the x-ray source 10 is rotated or moved. For example, eight projections may be captured to produce a basic 3-D data set by taking a projection every 45° of rotation around the ring 52. The quality of the resulting x-ray inspection data will improve as more projections are captured. By fixing the position of the apparatus with respect to the structure 4 a technician can control the apparatus to perform additional projections in order to capture more information regarding features and/or defects of the structure 4.

A computer or like processing device is used to transpose the x-ray projections captured by the x-ray detector into 3-D x-ray attenuation data, such as using commercially available or specialized software for digitally reconstructing a 3-D display of the inspection data for the structure under inspection. Generally, software using reconstruction algorithms such as Algebraic Reconstruction Technique (ART) are used to reconstruct projection data measured a various angles. The software combines the multiple focal plane slice images captured during the inspection to construct the 3-D x-ray attenuation data or 3-D display. By averaging corresponding data, reconstruction algorithms of the software minimize blurring of non-focal plane object structures that are superimposed as background data which would otherwise degrade the resolution of the inspection data. Further, averaging the combination of data from adjacent attenuations can provide estimates to generate a complete 3-D display of a structure.

The microfocus x-ray tube 10 is mounted at an angle on the circular racer bearing 54 to provide a constant incident angle for the inspection signal of the x-ray tube 10. Alternatively, an apparatus of an embodiment of the present invention may be designed to permit varying incident angles of inspection signals from an x-ray source. For example, an apparatus could provide the ability to rotate an x-ray source relative to a structure such as rotating the x-ray source 90° with respect to the structure to change the incident angle from 45° in one direction to 45° in the opposing direction.

Computed laminography is also possible with the present invention. By using magnetically coupled probes, an x-ray source and a corresponding x-ray detector can be simultaneously moved across opposing surfaces of a structure under inspection. Using reconstruction software, a computer can take advantage of the spread of the x-ray emission resulting in fin beam x-ray attenuation data. The reconstruction is capable of providing projections at a given location as the x-ray source and x-ray detector are moved across the structure.

In FIG. 2, another inspection apparatus performs x-ray laminography inspection of a that stringer structure 4. One difference between the embodiments shown in FIG. 2 and FIGS. 1A and 1B is that both the x-ray source 10 and the x-ray detector 12 are designed in the embodiment of FIG. 2 to move, such as to provide greater scanning area over the structure 4. One probe 6 of the apparatus is designed for being positioned across the that stringer 4 similar to the probes disclosed in co-pending application Ser. No. 11/041,499, entitled "Non-Destructive Stringer Inspection Apparatus and Method," filed Jan. 24, 2005. The probe 6 supports the x-ray source 10 which is fixed to a motion mechanism attached to the probe 6, which is a ring bearing 54 in FIG. 2, such as a ball or roller thrust bearing. Supports 50 which also function as radiation shields attach the x-ray source 10 to the ring bearing 54. The ring bearing 54 is rotatably connected to the probe 6 by a ring frame 52. A motor 55, controlled by a microcontroller 26 or a like device such as a computer, is used to control the movement of the x-ray source 10 by the rotation of the ring bearing 54. For example, a gear 52 attached to a motor 55 may engage the ring bearing 54 to permit controlled movement of the rotation of the x-ray source 10 by the microcontroller 26. Different methods can be used to control simultaneous rotation or motion of an x-ray source and an x-ray detector. For example, one or more microcontrollers can control corresponding smart stepper motors and communicate with positional encoders. Alternatively, for example, magnetic coupling devices can be used to create magnetic attraction between an x-ray source mounted on a circular racer bearing and an x-ray detector mounted on a corresponding circular racer bearing to provide magnetic attraction to move the x-ray source and x-ray detector when a motor moves one of the x-ray source and the x-ray detector.

A wireless transmitter 40 may be used with the microcontroller 26 to wirelessly control the probe 6, such as wirelessly controlling activation of the x-ray source 10, activation of a pump 28 to operate vacuum suction cups, and activation of the motor 55 to drive the rotation and position of the x-ray source 10. To create an apparatus which is entirely portable, each of the probes 6, 8 may include a battery 44 to power the electronic, mechanical, and electromechanical devices, such as a wireless transmitter 40, microcontroller 26, pump 28, motor 55, electromagnets, or other like devices.

Magnetically coupling devices 30 may be used to provide magnetic attraction between the probes 6, 8 to support the probes 6, 8 on opposing surfaces 4a, 4b, of the structure 4. Contact members 60 may be used to provide support of the probes 6, 8 on the opposing surfaces 4a, 4b and to permit the probes 6, 8 to move over the surfaces 4a, 4b when the probes 6, 8 are not fixed in position with respect to the structure 4, such as when pumps 28 are activated to operate and engage vacuum suction cups to the surfaces 4a, 4b. An example contact member 60 for use with vacuum suction cups 22 may include ball bearings 66 supported by recesses 64 that are spring biased by springs 62 thereby providing support for the probes 6, 8 when the vacuum suction cups 22 are not engaged and permitting the ball bearings 66 and recesses 64 to retract when the vacuum suction cups 22 are operated to engage the surfaces 4a, 4b.

The invention should not be limited to the specific disclosed embodiments. Specific terms are used in a generic and descriptive sense only and not for purposes of limitation.

The invention claimed is:

1. A non-destructive inspection apparatus for inspecting a structure, comprising:
    a first probe configured for being positioned on a first surface of the structure under inspection, the first probe comprising:
        at least one magnetic coupling device; and
        at least one x-ray source for emitting radiation for inspecting the structure when the first probe is positioned on the first surface of the structure, wherein the x-ray source is configured to provide inspection signals for performing an x-ray laminography inspection technique for inspecting the structure; and
    a second probe configured for being positioned on a second surface of the structure for through transmission inspection, the second probe comprising:
        at least one magnetic coupling device for magnetically coupling the second probe with the first probe, wherein the magnetic attraction of the magnetic coupling holds the first and second probes against the first and second surfaces of the structure; and
        at least one x-ray detector for receiving the radiation, wherein the x-ray detector is configured to provide x-ray data representing the received radiation for performing the x-ray laminography inspection technique for inspecting the structure.

2. The apparatus of claim 1, wherein the x-ray source and x-ray detector are configured to provide inspection signals and x-ray data, respectively, and wherein the inspection signals and x-ray data are for performing inspection of the structure using the x-ray laminography inspection technique selected from the group consisting of rotational-motion laminography, translational-motion laminography, complex-motion laminography, computed laminography, and multi-point laminography.

3. The apparatus of claim 1, wherein the first and second probes are further configured for traveling over the first and second surfaces of the structure, respectively, and wherein the probes cooperate by the magnetic coupling to move the respective magnetically coupled probe when the other probe is moved over the respective surface of the structure.

4. The apparatus of claim 3, wherein at least one probe further comprises a motor for moving the probes.

5. The apparatus of claim 1, wherein at least one probe further comprises a motion mechanism for supporting movement of one of the x-ray source or the x-ray detector.

6. The apparatus of claim 5, wherein the probe further comprises a motor for moving the x-ray source or the x-ray detector on the motion mechanism of the probe.

7. The apparatus of claim 1, wherein at least one probe further comprises a motor for moving one of the x-ray source or the x-ray detector of the probe.

8. The apparatus of claim 1, wherein the first probe is configured to permit adjustment of the incident angle of the radiation from the x-ray source with respect to the first surface of the structure.

9. The apparatus of claim 1, wherein at least one probe further comprises one or more vacuum suction cups for affixing the probe to the structure.

10. The apparatus of claim 1, wherein the magnetic coupling devices of the first and second probes are selected from the group consisting of a magnet and a ferromagnetic material insert.

11. The apparatus of claim 1, wherein the x-ray source comprises a microfocus x-ray tube and the x-ray detector comprises a CMOS x-ray detector.

12. The apparatus of claim 1, further comprising a display communicably coupled to the x-ray detector for presenting x-ray inspection images captured by the x-ray detector.

13. The apparatus of claim 1, wherein the x-ray detector comprises a wireless transmitter for transmitting x-ray inspection data.

14. A system for non-destructive inspection of a structure, comprising:
    a first probe configured for being positioned on a first surface of the structure under inspection, the first probe comprising:
        at least one magnetic coupling device; and
        at least one x-ray source for emitting radiation for inspecting the structure when the first
    probe is positioned on the first surface of the structure;
    a second probe configured for being positioned on a second surface of the structure for through transmission inspection, the second probe comprising:
        at least one magnetic coupling device for magnetically coupling the second probe with the first probe, wherein the magnetic attraction of the magnetic coupling holds the first and second probes against the first and second surfaces of the structure; and at least one x-ray detector for receiving the radiation and providing the received x-ray data for facilitating x-ray laminography inspection of the structure; and a processing device communicably coupled to the x-ray detector for receiving x-ray data and adapted to reconstruct the received x-ray data into a 3-D representation of the structure.

15. The system of claim 14, wherein the processing device is further adapted to control movement of the x-ray source and x-ray detector for performing x-ray laminography inspection of the structure.

16. The system of claim 14, wherein the processing device is further adapted to control movement of the probes for performing computed laminography as the probes move over the opposing surfaces of the structure.

17. The system of claim 14, further comprising a wireless transmitter communicably connected to the x-ray detector and a wireless receiver communicably connected to the processing device for permitting wireless communication of x-ray data from the x-ray detector to the processing device.

18. A method of inspecting a structure comprising:

supporting a first probe on a first surface of the structure and a second probe on an opposed second surface of the structure;

establishing magnetic attraction between the first and second probes sufficient for holding the probes on the first and second surfaces, respectively; and inspecting the structure using an x-ray laminography inspection technique, wherein the inspection comprises repeatedly transmitting x-ray inspection signals from an x-ray source carried by one probe into the structure and receiving signals following propagation through the structure with an x-ray detector carried by the other probe.

19. The method of claim 18, wherein the step of inspecting the structure further comprises moving the x-ray source in conjunction with repeatedly transmitting x-ray inspection signals to obtain multiple inspection projections of the structure.

20. The method of claim 19, wherein the step of moving the x-ray source comprises moving the x-ray source in at least one of the motion paths selected from the group consisting of rotational-motion, translational-motion, and complex-motion.

21. The method of claim 18, further comprising the step of moving one probe, wherein magnetic coupling between the probes causes the other probe to be moved along the opposing surface of the structure.

22. The method of claim 21, wherein the step of inspecting the structure is performed while the probes are moved along the structure, whereby the x-ray inspection technique is a computed laminography x-ray inspection technique to inspect the structure.

23. The method of claim 18, further comprising the step of displaying x-ray inspection data.

24. The method of claim 18, further comprising the step of wirelessly transmitting x-ray inspection data from the x-ray detector.

25. The method of claim 18, wherein the first probe comprises the x-ray source and the method further comprises the step of adjusting the incident angle of the inspection signals from the x-ray source with respect to the first surface of the structure, and, optionally, adjusting the angle of the x-ray detector corresponding to the adjustment of the incident angle of the inspection signals.

* * * * *

UNITED STATES PATENT AND TRADEMARK OFFICE
CERTIFICATE OF CORRECTION

| | | |
|---|---|---|
| PATENT NO. | : 7,050,535 B2 | Page 1 of 1 |
| APPLICATION NO. | : 11/045861 | |
| DATED | : May 23, 2006 | |
| INVENTOR(S) | : Georgeson et al. | |

It is certified that error appears in the above-identified patent and that said Letters Patent is hereby corrected as shown below:

Column 8,
Line 50, "that" should read --hat--.

Column 10,
Line 45, "fin" should read --fan--;
Lines 50 and 56, "that" should read --hat--.

Signed and Sealed this

Fourteenth Day of November, 2006

JON W. DUDAS
*Director of the United States Patent and Trademark Office*